ary Examiner—Vivian Garner
United States Patent [19]
Wan et al.

[11] 3,974,187
[45] Aug. 10, 1976

[54] SYNTHETIC ANALOGS HAVING THE ACTIVITY OF NATURALLY OCCURRING FORMS OF COENZYME Q

[76] Inventors: Yieh-Ping Wan, 1100 Reinli, Apt. 209, Austin, Tex. 78723; Karl Folkers, 6406 Mesa Drive, Austin, Tex. 78731

[22] Filed: Feb. 28, 1975

[21] Appl. No.: 553,927

[52] U.S. Cl. .............................. 260/396 R; 424/331
[51] Int. Cl.² ......................................... C07C 49/73
[58] Field of Search ................................ 260/396 R

[56] References Cited
UNITED STATES PATENTS 3,564,025  2/1971  Folkers et al. .................. 260/396 R
3,644,435  2/1972  Folkers et al. .................. 260/396 R

FOREIGN PATENTS OR APPLICATIONS 663,352   5/1963  Canada .......................... 260/396 R
927,531   5/1963  United Kingdom ............. 260/396 R
921,538   3/1963  United Kingdom ............. 260/396 R

*Primary Examiner*—Vivian Garner
*Attorney, Agent, or Firm*—Salvatore C. Mitri

[57] ABSTRACT

Synthetic 2,3-dimethoxy-5-methyl-1,4-benzoquinone is converted into a series of new 6-alkyl derivatives. These 6-alkyl derivatives have straight carbon chains which are both saturated and unsaturated. The unsaturated derivatives contain one, two, three and four double bonds. These new synthetic quinones are analogs of the naturally occurring forms of coenzyme Q and have the same fundamental electron-transfer capacity of the natural forms of coenzyme Q. Although the degree of the activity of these new synthetic analogs differ, some of these new synthetic analogs are effective substitutes for the natural forms of coenzyme Q.

8 Claims, No Drawings

SYNTHETIC ANALOGS HAVING THE ACTIVITY OF NATURALLY OCCURRING FORMS OF COENZYME Q

This invention relates to new, synthetically produced 6-alkyl derivatives of 2,3-dimethoxy-5-methyl-1,4-benzoquinone. These new 6-alkyl derivatives have the coenzymatic activities of the natural forms of coenzyme Q and specifically that of the form, coenzyme $Q_{10}$. More particularly, this invention relates to a process for synthesizing coenzymatically active analogs of the human coenzyme $Q_{10}$ which function in the electron-transfer mechanisms of respiration and coupled oxidative phosphorylation. These mechanisms are indispensable to mammalian life.

BACKGROUND OF THE INVENTION

The human form of coenzyme Q is coenzyme $Q_{10}$ (see formula below), and it is presumed to occur in every cell of every organ and every tissue of the human body which have mitochondria. Coenzyme $Q_{10}$ has the biological characteristics of a vitamin, and exists in human tissue in trace amounts as do the well-known vitamins. Coenzyme $Q_{10}$ occurs similarly in the tissue of cattle, and hundreds or thousands of hearts from cattle may be obtained from slaughter houses and used for the isolation of coenzyme $Q_{10}$ in pure form by a tedious and expensive process.

Coenzymes $Q_6$ through and including coenzyme $Q_{10}$ have been isolated from fermentations utilizing a variety of microorganisms. Again, these forms of coenzyme Q exist in trace amounts in fermentation materials and the isolation of the pure forms of coenzyme $Q_6 - Q_{10}$ from fermentation materials is a lengthy and costly process.

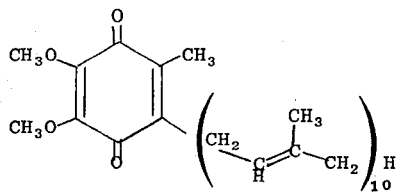

These naturally occurring forms of coenzyme Q exist in other living species including many of the higher plants. Again, the occurrence is in trace amounts and the isolation of a pure naturally occurring coenzyme Q from such other living source materials is a large-scale process.

The production of pure forms of the naturally occurring coenzymes $Q_6$ through $Q_{10}$ in kilogram or hundreds of kilogram quantities involves anenormous processing of slaughter house tissues, fermentation materials, higher plant an enormous fish wastes or other materials of living origin.

Certain synthetic modifications of coenzyme $Q_{10}$ have been found useful in the treatment of a human disease, i.e., periodontal disease. T. Matsummura, S. Saji, R. Nakamura and K. Folkers (*international J. Vit. Nutr. Research* 43, No. 4, 537–548 (1973).) produced evidence for the enhanced treatment of periodontal disease in humans by therapy with hexahydrocoenzyme $Q_4$. The synthesis of hexahydrocoenzyme $Q_4$ requires phytol which, in turn, is derived from the chlorophyll of plant tissue. Again, the dependence upon plant tissue is a disadvantage for hexahydrocoenzyme $Q_4$.

Both coenzyme $Q_{10}$ and hexahydrocoenzyme $Q_4$ showed hematological activity in nutritionally deficient children who were anemic. Such hematological activity of coenzyme $Q_{10}$ is potentially important in medicine as reported by A. S. Majaj and K. Folkers (*International J. Vit. Research* 38, No. 2, 182–195 (1968)).

The availability of the easy-to-synthesize, and on a very large scale, and relatively inexpensive 6-alkyl derivatives of 2,3-dimethoxy-5-methyl-1,4-benzoquinone which are coenzymatically active analogs of the naturally occurring forms of coenzyme Q will greatly facilitate new therapy in medicine.

The choice of the specific 6-substituted analog of the human coenzyme $Q_{10}$ to be used in medicine will depend not only upon reasonable costs and large-scale availability, but also on the route of therapeutic administration, duration of action and treatment, nature of the disease, and other variables. Consequently, not all of the various 6-alkyl, saturated and unsaturated, analogs will be equivalent or of equal potentiality for practical usage in medicine (veterinary or human). Some of these synthetic analogs will have advantages of usage over other analogs.

THE INVENTION

It has now been discovered, in accordance with the present invention, that new, synthetically produced 6-alkyl, saturated and unsaturated, analogs of the human coenzyme $Q_{10}$ are readily available, and in large quantity, and at a relatively low cost, which have the effective electron-transfer characteristics of coenzyme $Q_{10}$. It is well-known that coenzyme $Q_{10}$ is indispensable in the mammalian electron-transfer mechanisms of respiration and coupled oxidative phosphorylation. These new analogs are effective substitutes for coenzyme $Q_{10}$.

In accordance with the present invention, 2,3-dimethoxy-5-methyl-6-alkyl-1,4-benzoquinones are synthesized as follows. The 2,3-dimethoxy-5-methyl-1,4-benzoquinone is dissolved in acetic acid, and the appropriate diacyl peroxide is added. After reaction has taken place, the solution is concentrated in vacuo to dryness, and the residue is chromatographed. The 6-alkyl analogs, saturated and unsaturated, are appropriately obtained from the chromatographic purification and isolation.

The general procedure for synthesis of these 2,3-dimethoxy-5-methyl-6-alkyl-1,4-benzoquinones was as follows. To a solution of 10 mmoles of 2,3-dimethoxy-5-methyl-1,4-benzoquinone in 50 ml of acetic acid was added, in portions 20 to 30 mmoles of appropriate diacyl peroxide with stirring at 90°–100°C for 1–3 hours under nitrogen. The reaction mixture was heated for another 10–20 hours. The solution was concentrated, in vacuo, to dryness, and residue was subjected either to silica gel column chromatography with hexane and chloroform or to deactivated silica gel dry-column chromatography eluted with a mixture of hexane, chloroform and ether (10:10:1). The collected orange fraction was further purified on preparative thin layer plates developed with chloroform:hexane:ether (10:10:1) to collect the pure products. Elemental analyses are indicated only by symbols of the elements following the empirical formula. Analytical results obtained for those elements were with 0.4% of the theoretical values.

EXAMPLES

2,3-Dimethoxy-5-methyl-6-pentyl-1,4-benzoquinone

To a solution of 2,3-dimethoxy-5-methyl-1,4-benzoquinone (1.82 g; 10 mmol,) in 50 ml of glacial acetic acid at 90°–95°C under nitrogen was added portionwise over a 3-hour period a solution of dihexanoyl peroxide (6.9 g; 30 mmol) in 10 ml of glacial acetic acid. The resulting solution was maintained at 90°–95°C for 12 hours and cooled to room temperature. The solvent was removed in vacuo, and the residual oil was subjected to silica gel column chromatography eluted stepwise with solvent systems of increasing polarity from pure hexane to hexane-chloroform (6:4). Unreacted starting quinone (700 mg) was recovered as orange crystals. The orange band which travelled faster than the unreacted quinone, was collected and further purified by preparative thin layer chromatography developed with a mixture of hexane, chlorofrom and ether (10:10:1) to give a total of 510 mg of the pure desired product. Yield 33%. Anal. ($C_{14}H_{20}O_4$), C,H.

2,3-Dimethoxy-5-methyl-6-decyl-1,4-benzoquinone 2,3-Dimethoxy-5-methyl-1,4-benzoquinone (1.82 g., 10 mmol) was dissolved in 50 ml glacial acetic acid, and the mixture was heated to 90°–95°C under nitrogen. Then, a mixture of diundecanoyl peroxide (7.4 g., 20 mmol) in 5 ml of acetic acid was added dropwise over a 2-hour period. The reaction mixture was allowed to stir for another 20 hours at 90°–95°C, and then evaporated to dryness in vacuo. The residue was subjected to a silica gel column and eluted stepwise with solvent systems of increasing polarity from pure hexane to hexane-chloroform (6:4). The collected orange fraction was concentrated and further purified on the preparative thin layer plates developed with a mixture of chloroform: hexane: ether (10:10:1) to give a total of 1.4 g of pure product. Yield 43%. Anal. ($C_{19}H_{30}O_4$). C,H.

2,3-Dimethoxy-5-methyl-6-pentadecyl-1,4-benzoquinone

Dihexadecanoyl peroxide (4 g; 7.8 mmol) in 20 ml of glacial acetic acid was added portionwise to a stirred solution of 2,3-dimethoxy-5-methyl-1,4-benzoquinone (910 mg; 5 mmol) in 10 ml of glacial acetic acid at 90°–95° C under nitrogen. The reaction mixture was allowed to stir at 90°–95° C for 16 hours. The bright red solution turned yellow orange. The solvent was removed in vacuo and the residue was subjected to a silica gel column and eluted with a mixture of hexane and chloroform. The collected orange fraction was concentrated and further purified on the preparative thin layer plates developed with a mixture of chloroform: hexane: ether (10:10:1) to give 628 mg of pure product. Unreacted starting quinone (250 mg) was recovered as orange crystals; Yield 44%. Anal. ($C_{24}H_{40}O_4$) C,H.

2,3-Dimethoxy-5-methyl-6-(8'-pentadecyl)-1,4-benzoquinone

To a solution of 2,3-dimethoxy-5-methyl-1,4-benzoquinone (910 mg; 5 mmol) in 10 ml of glacial acetic acid at 90°–95° C under nitrogen was added portionwise over a 3-hour period a solution of dipalmitoleyl peroxide (2.5 g; 4.7 mmol) in 10 ml of glacial acetic acid. The resulting solution was maintained at 90°–95° C for 12 hours and cooled to room temperature. The solvent was removed in vacuo and the residual oil was subjected to deactivated silica gel dry-column chromatography eluted with a mixture of hexane, chloroform and ether (10:10:1). It was found that 350 mg of the unreacted starting quinone was recovered in addition to the alkylated quinone. The alkylated product which moved faster than the starting quinone down the column as an orange band was concentrated and further purified on preparative thin layer plates developed with a mixture of hexane, chloroform and ether (10:10:1) to give a total of 435 mg of the pure product; Yield 36%. Anal. ($C_{25}H_{40}O_4$). C,H.

2,3-Dimethoxy-5-methyl-6-(8'-heptadecenyl)-1,4-benzoquinone 2,3-Dimethoxy-5-methyl-1,4-benzoquinone (910 mg; 5 mmol) was dissolved in 10 ml of glacial acetic acid, and the mixture was heated at 95°–100°C under nitrogen. Then a solution of dioleoyl peroxide (2.5 g ; 6 mmol) in 10 ml of glacial acetic acid was added dropwise over a 2-hour period. The reaction mixture was allowed to stir for another 12 hours at 95°–100° C. The bright red solution became yellow orange. The resulting solution was evaporated to dryness in vacuo. The dark red residue was then subjected to deactivated silica gel dry-column chromatography eluted with a mixture of hexane, chloroform and ether (10:10:1). It was found that 324 mg of the starting 2,3-dimethoxy-5-methyl-1,4-benzoquinone were recovered in addition to the alkylated quinone. The alkylated product which moved faster than the starting quinone down the column as an orange band was concentrated and further purified on preparative thin layer plates developed with a mixture of hexane, chloroform and ether (10:10:1) to give a total of 595 mg of the pure product; Yield 46%. Anal. ($C_{26}H_{42}O_4$). C,H.

2,3-Dimethoxy-5-methyl-6-(8',11'-heptadecadienyl)-1,4-benzoquinone

To a solution of 2,3-dimethoxy-5-methyl-1,4-benzoquinone (910 mg; 5 mmol) in 10 ml of glacial acetic acid at 90°–95° C under nitrogen was added portionwise over a 3-hour period a solution of dilinoleyl peroxide (3.5 g; 6.25 mmol) in 10 ml of glacial acetic acid. The resulting solution was maintained at 90°–95° C for 12 hours and cooled to room temperature. The solvent was removed in vacuo and the residual oil was subjected to silica gel column chromatography eluted stepwise with solvent systems of increasing polarity from pure hexane to hexane-chloroform (6:4). The orange band, which travelled faster than the unreacted quinone, was collected and further purified by preparative thin layer chromatography developed with a mixture of hexane, chloroform and ether (10:10:1) to give a total 600 mg of the pure desired product. Unreacted starting quinone (160 mg) was recovered as orange crystals; Yield 35%. Anal. ($C_{26}H_{40}O_4$) C,H.

2,3-Dimethoxy-5-methyl-6-(8',11',14'-heptadecatrienyl)-1,4-benzoquinone

Dilinolenoyl peroxide (3.5 g; 6.25 mmol) in 10 ml of glacial acetic acid was added portionwise to a stirred solution of 2,3-dimethoxy-5-methyl-1,4-benzoquinone (910 mg; 5 mmol) in 10 ml of glacial acetic acid at 90°–95° C under nitrogen. The reaction mixture was allowed to stir at 90°–95° C for 16 hours. The bright red solution turned yellow orange. The solvent was removed in vacuo and the residue was subjected to chromatography on deactivated silica gel using a dry column technique eluted with a mixture of hexane, chloroform and ether (10:10:1). Unreacted 2,3-dimethoxy-5-methyl-1,4-benzoquinone (330 mg) was recovered in addition to the desired product. The alkylated quinone was collected and further purified on preparative thin layer plates developed with a mixture of hexane, chloroform and ether (10:10:1) to give a total of 310 mg pure product; Yield 24% Anal. ($C_{26}H_{38}O_4$). C,H.

2,3-Dimethoxy-5-methyl-6-(10'-nonadecenyl)-1,4-benzoquinone 2,3-Dimethoxy-5-methyl-1,4-benzoquinone (910 mg; 5 mmol) was dissoled in 10 ml of glacial acetic acid, and the mixture was heated at 90°–95° C under nitrogen. Then a solution of di(11'-eicosenoyl) peroxide (2.18 g; 3.5 mmol) in 10 ml of glacial acetic acid was added dropwise over a 2-hour period. The reaction mixture was allowed to stir for another 18 hours at 90°–95° C. The resulting solution was evaporated to dryness in vacuo. The dark red residue was then subjected to dry column chromatography on silica gel eluted with a mixture of hexane, chloroform and ether (10:10:1). A total of 260 mg pure product was obtained as an orange oily material; Yield 24%. Anal. ($C_{28}H_{46}O_4$). C,H.

2,3-Dimethoxy-5-methyl-6-10',13'-nonadecadienyl)-1,4-benzoquinone

To a solution of 2,3-dimethoxy-5-methyl-1,4-benzoquinone (700 mg; 3.8 mmol) in 5 ml of glacial acetic acid at 90°–95° C under nitrogen, di-(11',14'-eicosadienoyl) peroxide (2.27 g; 3.7 mmol) in 25 ml of acetic acid was added dropwise over a 3-hour period. The resulting solution was maintained at 90°–95° C for 12 hours and cooled to room temperature. The solvent was removed in vacuo and the residue was chromatographed on deactivated silica gel using the dry column technique, eluted with a mixture of hexane, chloroform and ether (10:10:1). The purest fraction was rechromatographed on preparative thin layer plates developed with the mixture of hexane, chloroform and ether (10:10:1) to yield a total of 237 mg of pure product. Unreacted 2,3-dimethoxy-5-methyl-1,4-benzoquinone (280 mg) was recovered as red orange crystals. Yield 23%. Anal. ($C_{28}H_{44}O_4$). C,H.

2,3-Dimethoxy-5-methyl-6-(10',13',16'-nonadecatrienyl)-1,4-benzoquinone

Di(11',14',17'-eicosatrienoyl)-peroxide (2.16 g; 3.5 mmol) in 20 ml of glacial acetic acid was added dropwise to a stirred solution of 2,3-dimethoxy-5-methyl-1,4-benzoquinone (700 mg; 3.8 mmol) in 2-3 ml of glacial acetic acid at 90°–100° C under nitrogen. After the addition was completed, the reaction mixture was allowed to stir at 90°–100° C for another 12 hours. The bright red solution became yellow orange. The solvent was removed in vacuo and the residue was chromatographed on a deactivated silica gel dry column eluted with a mixture of hexane, chloroform and ether (10:10:1). A total of 403 mg pure product was obtained as an orange oily material. Yield 31%. Anal. ($C_{28}H_{40}O_4$).C,H.

2,3-Dimethoxy-5-methyl-6-n-eicosyl-1,4-benzoquinone 2,3-Dimethoxy-5-methyl-1,4-benzoquinone (910 mg; 5 mmol) was dissolved in 20 ml of glacial acetic acid, and the mixture was heated at 90°–95°C with stirring under nitrogen. A suspension of diheneicosanoyl peroxide (4 g; 6.2 mmol) was added portionwise to the reaction mixture over a 3-hour period. The reaction mixture was allowed to stir for another 14 hours at 90°–95°C and evaporated to dryness in vacuo. The dark red residue was then subjected to dry-column chromatography eluted with a mixture of hexane, chloroform and ether (10:10:1). It was found that 410 mg starting 2,3-dimethoxy-5-methyl-1,4-benzoquinone was recovered in addition to the alkylated quinone, which travelled faster than the unreacted quinone down the column as an orange band, was rechromatographed on preparative thin layer plates. A mixture of hexane, chloroform and ether (10:10:1) was used to develop the plates. 2,3-Dimethoxy-5-methyl-6-n-eicosayl-1,4-benzoquinone (280 mg) was obtained as yellow solid material as the solvents evaporated. Yield 22% m.p. 65°–66°C. Anal. ($C_{24}H_{50}O_4$) C,H.

2,3-Dimethoxy-5-methyl-6-(4',7',10',13'-nonadecatetraenyl)-1,4-benzoquinone.

Diarachidonoyl peroxide (2 g; 3.2 mmol) in 20 ml of glacial acetic acid was added portionwise to a stirred solution of 2,3-dimethoxy-5-methyl-1,4-benzoquinone (700 mg; 3.8 mmol) in 5 ml of glacial acetic acid at 95°–100°C under nitrogen. The reaction mixture was allowed to stir at 95°–100°C for 12 hours. The resulting solution was cooled and the solvent was removed in vacuo. The residual oil was subjected to deactivated silica gel dry-column chromatography eluted with a mixture of hexane, chloroform and ether (10:10:1). The alkylated quinone which moved faster than the starting quinone down the column as an orange band was concentrated and further purified on preparative thin layer plates developed with the same solvent mixture used for dry column chromatography to give 35.5 mg desired product. Anal. ($C_{28}H_{40}O_4$) C,H.

BIOLOGICAL EVALUATION: TABLE I

The CoQ activity of each analog was assessed by examining the ability of the analog to stimulate the succinoxidase activity of beef-heart mitochondria (BHM) from which the naturally occurring CoQ had been removed by pentane extraction. (Table I) Beef heart mitochondria were prepared by the method of Smith (Methods Enzymol., 10, 81 (1967). The pentane extraction was conducted as described by Szarkowska (Arch. Biochem. Biophys., 113, 519 (1966); PEBHM was frozen and used within 10 days of preparation, since pentane extraction decreases the stability of BHM. Succinoxidase activity was determined manometercally, using a Gilson differential respirometer (Iwamoto, Y., Hansen, I. L., Porter, T. H., and Folkers, K., Biochem. Biophys. Res. Comm., 58, 633 (1974), and is reported as microatmospheres of oxygen per minute per milligram of protein. A commercial soybean phospholipid preparation (Asolectin), dispersed by sonication (Fleischer, S. and Fleischer, B., Methods Enzymol., 10, 421 (1967), was used to provide phospholipid micelles, and test substances were added as solutions in ethanol.

Within Table I are listed the CoQ activities of the analogs and selected reference compounds. The $CoQ_{10}$ Activity Index is a measure of the effectiveness of the analogs, relative to the standard, in stimulating a submaximal response of succinoxidase activity. Specific activity of the succinoxidase system in response to stimulation by exogenous $CoQ_{10}$ is given in footnote a of the Table. The quantity of analog to be added was chosen to provide a level of succinoxidase activity corresponding to the nearly linear portion of the activity: dose curve, in which succinoxidase activity stimulated is approximately proportional to the level of analog used. The second column lists the nanomolar quantity of analog required to provide a stimulation of about half of the maximum response. The relative response of the succinoxidase system to 400 nmol of each analog is listed in the third column of the Table. This level of analog is sufficient to insure significant excess over the stoichiometric amount, and maximum response to $CoQ_4$ is obtained at one-tenth to one-twentieth of this dose level. The response to 400 nmol of $CoQ_{10}$ is lower than is the response to other components listed. The very long side-chain of $CoQ_{10}$, the natural coenzyme, may hinder the transport of exogenous $CoQ_{10}$ to the active site.

TABLE I.

CoQ ACTIVITY OF 6-ALKYL-2,3-DIMETHOXY-5-METHYL-1,4-BENZOQUINONES
IN THE SUCCINOXIDASE SYSTEM OF BEEF HEART MITOCHONDRIA

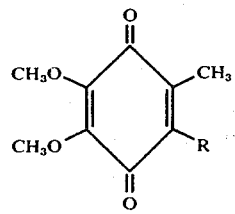

| Compounds | CoQ Activity[a] | | |
|---|---|---|---|
| | Relative[b] Effectiveness | $CoQ_{10}$[c] Act. Index | Maximum[d] Activation |
| $CoQ_{10}$ (Standard) | 4.8 | 1.0 | 78 |
| $CoQ_4$ | 100. | 20.8 | 100 |
| $H_6CoQ_4$ | 10.3 | 2.2 | 95 |
| $CoQ_7$ | 8.2 | 1.7 | 90 |
| 2,3-Dimethoxy-5-Methyl-1,4-Benzoquinone: | | | |
| R = Pentyl ($-(CH_2)_4CH_3$) | 5.7 | 1.2 | 86 |
| Decyl ($-(CH_2)_9CH_3$) | 56. | 11.7 | 96 |
| Pentadecyl ($-(CH_2)_{14}CH_3$) | 21. | 4.4 | 94 |
| Eicosyl ($-(CH_2)_{19}CH_3$) | 4.5 | 0.9 | 62 |
| 8'-Pentadecenyl ($-(CH_2)_7CH=CH(CH_2)_5CH_3$) | 58. | 11.1 | 93 |
| 8'-Heptadecenyl ($-(CH_2)_7CH=CH(CH_2)_7CH_3$) | 28. | 5.8 | 94 |
| 8',11'-Heptadecadienyl ($-(CH_2)_7(CH=CHCH_2)_2(CH_2)_3CH_3$) | 43. | 9.0 | 95 |
| 8',11',14'-Heptadecatrienyl ($-(CH_2)_7(CH=CHCH_2)_3CH_3$) | 60. | 12.5 | 96 |
| 10'-Nonadecenyl ($-(CH_2)_9CH=CH(CH_2)_7CH_3$) | 28. | 5.8 | 96 |
| 10',13'-Nonadecadienyl ($-(CH_2)_9(CH=CHCH_2)_2(CH_2)_3CH_3$) | 35. | 7.3 | 96 |
| 10',13',16'-Nonadecatrienyl ($-(CH_2)_9(CH=CHCH_2)_3CH_3$) | 49. | 10.2 | 100 |
| 4',7',10',13'-Nonadecatetraenyl ($(CH_2)_3(CH=CHCH_2)_4(CH_2)_3CH_3$) | 37. | 7.7 | 92 |

[a]The activities of the compounds in restoring the succinoxidase activity of pentane-extracted beef heart mitochondria (PEBHM) were determined manometrically. The CoQ content of the beef heart mitochondria was 3.46 nmol of $CoQ_{10}$/mg protein, before pentane extraction. For each determination, the quantity of protein used was 0.65–0.85 mg of PEBMH.
[b]Relative effectiveness was calculated by comparing the molar amounts of analog and $CoQ_4$ required to restore the same level of succinoxidase to the PEBHM; effectiveness is expressed as percent, relative to $CoQ_4$.
[c]The activity index was calculated from the relative effectiveness, and expresses the activity of the analog in terms of that of $CoQ_{10}$.
[d]The activity of the enzyme which is restored upon addition of an excess molar quantity of the analog (400 nm of analog per flask) is listed as percent of the response to $CoQ_4$.

TABLE II.

CoQ ACTIVITY OF 6-ALKYL DERIVATIVES OF
2,3-DIMETHOXY-5-METHYL-1,4-BENZOQUINONE
IN THE SUCCINOXIDASE SYSTEM OF BEEF HEART MITOCHONDRIA

| Compounds | CoQ Activity[a] | |
|---|---|---|
| | Estimated nMoles Required for 50% Activation[b] | Activation at 400 nMoles %[c] |
| $CoQ_{10}$ (Standard) | (3.46, 41.7 | no activation)[d] 100 |
| $H_6CoQ_4$ | 19.4 | 121 |
| $CoQ_7$ | 24.4 | 115 |

TABLE II.-continued

CoQ ACTIVITY OF 6-ALKYL DERIVATIVES OF 2,3-DIMETHOXY-5-METHYL-1,4-BENZOQUINONE IN THE SUCCINOXIDASE SYSTEM OF BEEF HEART MITOCHONDRIA

| Compounds | CoQ Activity[a] | |
|---|---|---|
| | Estimated nMoles Required for 50% Activation[b] | Activation at 400 nMoles %[c] |
| $CoQ_4$ | 2.0 | 128 |
| 2,3-Dimethoxy-5-Methyl-1,4-Benzoquinone: | | |
| R = Pentyl | 35.1 | 110 |
| Decyl | 3.6 | 123 |
| Pentadecyl | 9.5 | 121 |
| Eicosyl | 44.4 | 79 |
| 8'-Pentadecenyl | 3.4 | 119 |
| 8'-Heptadecenyl | 7.1 | 121 |
| 8', 11'-Heptadecadienyl | 4.7 | 122 |
| 8', 11', 14'-Heptadecatrienyl | 3.3 | 123 |
| 10'-Nonadecenyl | 7.1 | 123 |
| 10', 13'-Nonadecadienyl | 5.7 | 123 |
| 10', 13', 16'-Nonadecatrienyl | 4.1 | 128 |
| 4', 7', 10', 13'-Nonadecatetraenyl | 5.4 | 118 |

[a]The activities of the compounds in restoring the succinoxidase activity of pentane-extracted beef heart mitochondria (PEBHM) were determined nanometrically. The CoQ content of the beef heart mitochondria was 3.46 nmoles of $CoQ_{10}$/mg protein, before pentane extraction. For each determination, the quantity of protein used was 0.65–0.85 mg of PEBHM.
[b]The values listed are the levels of the analogs required to reinstate approximately 50% of the maximum activity of the succinoxidase system.
[c]Responses of the succinoxidase system to stimulation by 400 nmoles of the analog is listed, relative to the response to 400 nmoles $CoQ_{10}$.
[d]The specific activities of the enzyme system in response to various doses of $CoQ_{10}$ are: (nmoles $CoQ_{10}$/flask, Specific Activity) 0, 0.52; 10, 0.160; 20, 0.248; 30, 0.298; 40, 0.344; 100, 0.488. Full restoration of activity of succinoxidase in PEBHM was observed in response to more than 20 nmoles of $CoQ_4$; the maximum activity was 0.700 μatm $O_2$/mg protein min.

The data in Table I show calculations, based on the direct biochemistry of the CoQ activity of the 6-alkyl-2,3-dimethoxy-5-methyl-1,4-benzoquinones in the succinoxidase system of beef heart mitochondria. The data in Table II, are based upon the very same data which led to Table I, but the calculations in Table II permit direct interpretation of the relative usefulness of these new 6-alkyl derivatives in human medicine. Such interpretation, based on the data and calculations of Table II are as follows.

The human coenzyme $Q_{10}$ may be viewed as the "standard", because it exists and functions in human tissue, and is the baseline for the improvements and discovery of this invention. Table II shows that coenzyme $Q_{10}$ is poorly utilized in this mitochondrial in vitro system, and it is understood that the oral absorption of $CoQ_{10}$ by the human is likewise inefficient. Even in the dying nutritionally dystrophic rabbit, which is deficient in coenzyme $Q_{10}$, the administration of coenzyme $Q_{10}$ failed to elicit therapeutic activity and save the life of the rabbit, although rabbit tissue like human tissue naturally utilizes coenzyme $Q_{10}$. This failure of the dying rabbit to respond to coenzyme $Q_{10}$, according to T. M. Farley, G. D. Daves, Jr., J. Scholler, and K. Folkers (*International J. for Vit. Res.* 38, No. 3–4, 1968), was explained on the basis of ineffective transport of coenzyme $Q_{10}$ from intravenous administration to the enzyme sites where the functionality of coenzyme $Q_{10}$ is essential. Table II shows that at high levels (41.7 nMoles) of coenzyme $Q_{10}$, there is maximum activation of succinoxidase.

The data in Table II show that of the four CoQ's, $CoQ_{10}$, $H_6CoQ_4$, $CoQ_7$ and $CoQ_4$, only that one of these four CoQ's, which has a low molecular weight ($CoQ_4$), is effectively utilized by succinoxidase in this mitochondrial system. Also, it is seen that $CoQ_4$ can elicit maximum activation of succinoxidase. $CoQ_{10}$, $H_6CoQ_4$, $CoQ_7$ and $CoQ_4$ all suffer from the disadvantage, as explained elsewhere in this disclosure, of being derived fully or partially from natural source materials and by high-cost procedures.

Table II shows that the 6-n-pentyl derivative is about as little effective as coenzyme $Q_{10}$ itself, but in this case the explanation is because the pentyl side chain is too low in lipoidal characteristics to be efficiently functional in this system. This relatively ineffective 6-n-pentyl derivative may be compared with the relatively ineffective coenzyme $Q_3$ which did not save the life of the dying dystrophic rabbit, because of its minimally effective side chain, according to Farley, et al., cited above.

The data in Table II show that the 6-n-decyl derivative is effective, but effectiveness decreases as the decyl group (10 carbons) is changed to pentadecyl (15 carbons) and to eicosyl (20 carbons). The eicosyl derivative has another disadvantage in this system in that it cannot stimulate maximum activation.

The data in Table II show very important results when two groups of three 6-alkyl derivatives in each group are compared. The two groups are the 8'-heptadecenyl, 8',11'-heptadecadienyl, and 8',11',14'-heptadecatrienyl. The three derivatives in the second group are the 10'-nonadecenyl, 10'13'-nonadecadienyl, and 10',13',16'-nonadecatrienyl derivatives. For both of these groups of three derivatives each, it is evident that increasing unsaturation (one and two and three double bonds) increases the effectiveness of the derivative to activate the enzyme, because a smaller amount is needed to achieve essentially equivalent activations as the unsaturation increases.

The data in Table II show that there is a little additional effectiveness to be gained from the 4',7',10'13'-nonadecatetraenyl over the 10'13'16'-nonadecatrienyl derivatives.

All data in Table II bear upon medical applications in human disease.

For over ten years, synthetic lower homologs of coenzyme Q such as $CoQ_1$, $CoQ_2$ and $CoQ_3$ have been internationally useful in biochemical experimentation as may be documented by many publications in the biochemical literature.

The relative chemical instability of low molecular weight isoprenoid quinones including $CoQ_1$, $CoQ_2$ and $CoQ_3$, can be a difficulty and partially decomposed samples can be inadvertently used and presumed to be satisfactory. An extreme example is plastoquinone-3 which was surprisingly and extremely unstable, according to D. Misiti, H. W. Moore, and K. Folkers (*J. Amer. Chem. Soc.* 87, 1402, 1965).

To circumvent the potential and frequently overlooked aspect of instabilities of $CoQ_1$ and $CoQ_2$ and $CoQ_3$, two new analogs have been synthesized where the isoprenoid groups of $CoQ_1$ and $CoQ_2$ are replaced with saturated straight-chain alkyl groups. In other words, the 6-n-pentyl derivative "simulates" $CoQ_1$, and the 6-n-decyl derivative "simulates" $CoQ_2$. Biological evaluation, in vitro, on the new 6-n-pentyl and 6-n-decyl and on the previously known 6-n-pentadecyl derivatives of 2,3-dimethoxy-5-methyl-1,4-benzoquinones are summarized in the following paragraphs from Y. P. Wan, R. H. Williams, K. Folkers, K. H. Leung, and E. Racker in *Biochem. Biophys. Res. Comm.*, 63, 1975.

Biological Evaluation (Tables III and IV)

2,3-Dimethoxy-5-methyl-6-n-pentyl-1,4-benzoquinone (PB) and the corresponding 6-n-decyl-derivative (DB) were as biochemically effective as $CoQ_1$ in the systems used, as indicated in Table III. The corresponding 6-n-pentadecyl-derivative (PDB) was not suitable or as effective, because of its lower solubility in water. In this assay system, $CoQ_{10}$ is also too insoluble and even the somewhat more soluble $CoQ_6$ is not adequate.

One may observe that any biochemical assay system, in vitro, for research on respiration, in which the intrinsic role of coenzyme Q is important, must necessarily be responsive to forms and analogs of coenzyme Q which are sufficiently lipoidal in nature. The lipoidal nature of the analog permits simulation of the intrinsic coenzyme Q for both coenzymatic activity and for inhibition. However, a form or analog of coenzyme Q with negligible or minimal lipoidal character, and an assay system which is not responsive to the lipoidal analogs and forms of CoQ, can give very useful biochemical information. Such information may or may not bear directly on the intrinsic role of the dominant form of coenzyme Q in the given species, i.e., $CoQ_6$ or $Q_7$ in yeast, $CoQ_8$ in E. coli., $CoQ_{10}$ in mammalian mitochondria, etc.

The apparent greater stability of PB and DB and the observation that they serve as well as $CoQ_1$ in this assay for oxidative phosphorylation at site I, document their utility. Also, after reduction and extraction, both PB and DB were excellent substrates in the assay with complex III. It can be seen from Table IV that both gave very low blank reduction of cytochrome $c$ and reacted as well as $CoQ_1$ and $CoQ_2$ with complex III. Again, this system of complex III was virtually unresponsive to the 6-n-pentadecyl derivative, and there was no inhibition, and doubtless because of the increased lipoidal nature of this 15-carbon (side chain) analog in comparison with that of the 5- and 10-carbon analogs, PB and DB, respectively. It could be misleading to consider the pentadecyl-derivative "inactive" in this system of complex III, because the analog is as potentially functional in redox reactions as are the pentyl- and decyl-derivatives. Such "inactivity" is really due to the incompatibility of the assay system with the more lipoidal analog.

Table III

| CoQ or Analog 0.12 nM | $\mu$moles NADH /min/mg | $\mu$moles NADH min/mg +Rotenone | % Inhibition by Rotenone | $\Delta$ NADH | $\Delta$ G6P | P/NADH Ratio |
|---|---|---|---|---|---|---|
| $Q_1$ | 0.45 | 0.03 | 93% | 0.088 | 0.046 | 0.522 |
| $Q_2$ | 0.25 | 0.02 | 92% | 0.079 | 0.045 | 0.57 |
| PB | 0.47 | 0.02 | 95% | 0.082 | 0.036 | 0.44 |
| DB | 0.52 | 0 | 100% | 0.085 | 0.039 | 0.46 |

Assays were performed with 200 $\mu$g of ETPH particles as described by Schatz and Racker (J. Biol. Chem., 241, 1429 (1966)). The concentration of the CoQ compounds was 0.12 mM. Rotenone was added at 2 $\mu$M concentration.

TABLE IV

REDUCTION OF CYTOCHROME c REDUCED COQ AND ANALOGS CATALYZED BY COMPLEX III

| Reduced CoQ or Analog | Non-enzymatic Rate of Cytochrome c Reduction (nmoles/min) | nMoles Cytochrome c Reduced/min | % Inhibition by Antimycin A |
|---|---|---|---|
| $Q_1$ | 0.6 | 12.4 | 100 |
| $Q_2$ | 0.2 | 27.4 | 98 |
| PB | 0.2 | 14.6 | 100 |
| DB | 0.2 | 29.0 | 98 |

Reduction of cytochrome c was measured at 550–540 nm. The reaction mixture contained in 1.0 ml: 25 nM $KP_i$, pH 7.5; 0.05 mM EDTA; 8 $\mu$M cytochrome $c_i$; 10 $\mu$M reduced CoQ or analog and 2 $\mu$g complex III. When indicated, antimycin A was added to the assay medium at 1 $\mu$g/ml. An extinction coefficient of 19 $mM^{-1}$ was used for reduced cytochrome c.

It is clearly evident from the data in Tables III and IV and the information in the paragraphs under the heading Biological Evaluation (Tables III and IV that the pentyl and decyl analogs are highly effective as evidenced by their functioning like $CoQ_1$ and $CoQ_2$ as hydrogen acceptors with ETPH particles for oxidative phosphorylation at site I, and after reduction as hydrogen donors for complex III. The 6-n-pentyl and 6-n-decyl derivatives of 2,3-dimethoxy-5-methyl-1,4-benzoquinone are effective in biochemical assays and particularly are superior to $CoQ_1$ and $CoQ_2$ in chemical stability, ease of synthesis, storage, and general utility.

As evidence of the usefulness of the new pentyl and decyl derivatives, the two inventors of this application have given away on request more than 20 samples to more than 10 investigators in as many states and countries. This demand for samples is expected to increase greatly when it becomes generally known after March 1975 that the pentyl and decyl derivatives are available, useful, and superior to $CoQ_1$ and $CoQ_2$.

In summary, these new 6-n-alkyl, saturated and unsaturated, derivatives of 2,3-dimethoxy-5-methyl-1,4-benzoquinone are useful, relatively inexpensive, straightforward to synthesize, and superior quinones in comparison with the naturally occurring forms of coenzyme Q. These new 6-n-alkyl quinones, which have the same electron-transfer characteristics as the naturally occurring forms of coenzyme Q, are useful and necessary in many biochemical experiments in laboratories. It is expected that the pentyl and decyl derivatives will be placed on the market for such purpose, because of their utility as described by Y. P. Wan. R. H. Williams, K. Folkers, K. H. Leung, and E. Racker in *Biochem. Biophys. Res. Commun.*, 63, 1975. Those 6-n-alkyl derivatives with side chains of ten and more carbon atoms, which are both saturated and unsaturated, will be advantageous over naturally occurring forms of coenzyme Q for treatment of human diseases which have already shown responses to naturally occurring forms of coenzyme Q. Even these new 6-n-alkyl derivatives of ten and more carbon atoms, saturated and unsaturated, are useful in laboratory experimentations in biochemistry and in nutritional sciences as are the pentyl and decyl derivatives as described by Wan et al., in the above citation.

Our examples illustrate synthesis of the new 6-alkyl analogs, and particularly the unsaturated ones, which are representative and not restrictive.

What is claimed:

1. 6-Alkenyl-2,3-dimethoxy-5-methyl-1,4-benzoquinones where the 6-alkenyl groups are n-(8'-pentadecenyl), n-(8'-heptadecenyl), n-(8', 11'-heptadecadienyl), n-(8', 11', 14'-heptadecatrienyl), n-(10'-nonadecenyl), n-(10', 13'-nonadecadienyl), and n-(10', 13', 16'-nonadecatrienyl).

2. The quinone compound of claim 1 wherein the 6-alkenyl group is n-(8'-pentadecenyl).

3. The quinone compound of claim 1 wherein the 6-alkenyl group is n-(8'-heptadecenyl).

4. The quinone compound of claim 1 wherein the 6-alkenyl group is n-(8',11'-heptadecadienyl).

5. The quinone compound of claim 1 wherein the 6-alkenyl group is n-(8',11',14'-heptadecatrienyl).

6. The quinone compound of claim 1 wherein the 6-alkenyl group is n-(10'-nonadecenyl).

7. The quinone compound of claim 1 wherein the 6-alkenyl group is n-(10',13'-nonadecadienyl).

8. The quinone compound of claim 1 wherein the 6-alkenyl group is n-(10',13',16'-nonadecatrienyl).

* * * * *